(12) United States Patent
Truwit et al.

(10) Patent No.: US 6,802,323 B1
(45) Date of Patent: Oct. 12, 2004

(54) METHOD AND APPARATUS FOR STORING GUIDE WIRES

(75) Inventors: Charles L. Truwit, Wayzata, MN (US); Randal Nebon, Pine Springs, MN (US)

(73) Assignee: iSurgical, LLC, St. Paul, MN (US)

( * ) Notice: Subject to any disclaimer, the term of this patent is extended or adjusted under 35 U.S.C. 154(b) by 0 days.

(21) Appl. No.: 09/849,791

(22) Filed: May 4, 2001

Related U.S. Application Data
(60) Provisional application No. 60/203,094, filed on May 5, 2001.

(51) Int. Cl.$^7$ ............................................. B08B 3/04
(52) U.S. Cl. ................... 134/117; 134/120; 134/151; 134/186
(58) Field of Search ................... 134/166 C, 169 C, 134/168 C, 151, 186, 117, 118, 119, 120; 396/628, 631, 642, 643, 644; 433/79, 77

(56) References Cited

U.S. PATENT DOCUMENTS

| | | | | |
|---|---|---|---|---|
| 289,951 | A | * | 12/1883 | Davis |
| 503,144 | A | * | 8/1893 | Kem et al. |
| 616,152 | A | * | 12/1898 | Smith |
| 620,224 | A | * | 2/1899 | Bubser |
| 907,942 | A | * | 12/1908 | Zierath |
| 979,858 | A | * | 12/1910 | Hotze |
| 1,135,503 | A | * | 4/1915 | Crawford |
| 1,444,435 | A | * | 2/1923 | Steinberger |
| 2,037,081 | A | * | 4/1936 | Manning |
| 2,192,940 | A | * | 3/1940 | Smith |
| 2,268,454 | A | * | 12/1941 | Moore |
| 2,807,513 | A | * | 9/1957 | Stein |
| 2,910,076 | A | * | 12/1959 | McNett |
| 3,055,378 | A | * | 9/1962 | Alford |
| 3,078,575 | A | * | 2/1963 | Fontana |
| 3,459,202 | A | * | 8/1969 | Roberson |
| 3,555,990 | A | * | 1/1971 | Dittman |
| 3,634,937 | A | * | 1/1972 | Green |
| 4,198,153 | A | * | 4/1980 | Hamlin |
| 4,332,455 | A | * | 6/1982 | Stettner |
| 4,379,467 | A | * | 4/1983 | Purr |
| 5,279,317 | A | * | 1/1994 | Bowman et al. |
| 5,549,759 | A | * | 8/1996 | Lithander |
| 5,709,235 | A | * | 1/1998 | Akanuma et al. |
| 5,819,770 | A | * | 10/1998 | Randall et al. |
| 5,848,693 | A | * | 12/1998 | Davis et al. |
| 5,906,802 | A | * | 5/1999 | Langford |
| 6,047,825 | A | | 4/2000 | Samuels ..................... 206/364 |
| 6,095,162 | A | * | 8/2000 | Miller et al. |

FOREIGN PATENT DOCUMENTS

FR          2364014          *    4/1978

\* cited by examiner

*Primary Examiner*—Frankie L. Stinson
(74) *Attorney, Agent, or Firm*—Schwegman, Lundberg, Woessner & Kluth, P.A.

(57) ABSTRACT

A guide wire holding apparatus includes a tray, one or more raised corrugated areas, a fluid source, a syringe, a valve, a drainage system, and one or more coupling devices. Each of the one or more raised corrugated areas is located on the inner surface of the tray and includes one or more slots. A reservoir is formed by the inner surface of the tray and the tray end caps. A flow of fluid provided by the fluid source or the syringe and controlled by the valve partially fills the reservoir. The height of the fluid in the reservoir is partially controlled by the location of the cap hole. Preferably, the cap hole is located at a height that causes the guide wire, which is shown resting in a slot formed in the one or more raised corrugated areas, to be slightly submerged when fluid is flowing from the fluid source or syringe to the drainage system.

5 Claims, 3 Drawing Sheets

METHOD AND APPARATUS FOR STORING GUIDE WIRES

CROSS REFERENCE TO RELATED APPLICATION

This application claims the benefit under 35 U.S.C. 119(e) from U.S. Provisional Application Ser. No. 60/203,094, filed May 5, 2000, which is hereby incorporated by reference.

FIELD

This invention relates to surgical trays, and more particularly to surgical trays that are useful for temporarily storing catheters and guide wires during a surgical procedure.

BACKGROUND OF THE INVENTION

Some surgical procedures require the use of catheters and guide wires. In the United States alone, thousands of procedures using catheters and guide wires are performed each year. The catheters and guide wires used in these procedures may be temporarily stored in a surgical tray and reused during the procedure. The surgical tray is typically located behind the physician, and turning to store the guide wires or catheters can temporarily distract the physician and increase the patient's risk during the operation.

For example, when an angiography is performed, typically a catheter is inserted into the femoral artery over a guide wire (and often through a previously placed arterial sheath). The guide wire is often used in conjunction with the catheter for the purposes of manipulation and safe advancement of the catheter into a vessel lumen. Once the catheter tip is advanced to the appropriate location, the guide wire is removed, the catheter is flushed, and a test injection is often made with angiographic dye. Upon removing the guide wire, the angiographer is confronted with a situation where she has to turn her back on the patient for a few moments to place the guide wire in a basin containing heparinized saline. This is done to keep the guide wire moist so that a low coefficient of friction is maintained when the guide wire is reinserted into the catheter for subsequent uses. Often, the guide wire needs to be coiled to fit in the basin or needs to be reinserted into a guide wire plastic sleeve, which typically contains heparinized saline. Coiling the guide wire or reinserting the guide wire into a guide wire plastic sleeve requires some manual dexterity and time to clean and coil the guide wire or insert the guide wire into the guide wire sleeve. During these activities the angiographer is not focused on the patient.

For these and other reasons there is a need for the present invention.

SUMMARY OF THE INVENTION

The present invention provides a method and apparatus for storing and retrieving a guide wire. According to one embodiment of the invention, an apparatus for storing a guide wire comprises a tray having an inner surface, and one or more raised corrugated areas located on the inner surface. According to an alternate embodiment of the invention, a method for temporarily storing and retrieving the guide wire includes placing the guide wire in a slot formed in a raised corrugated area, such as a corrugated bar, and removing the guide wire from the tray by grasping a section of the guide wire separated from the inner surface of the tray by the guide wire storage solution. These and various other embodiments of the invention are described below.

DETAILED DESCRIPTION

Figure 1:
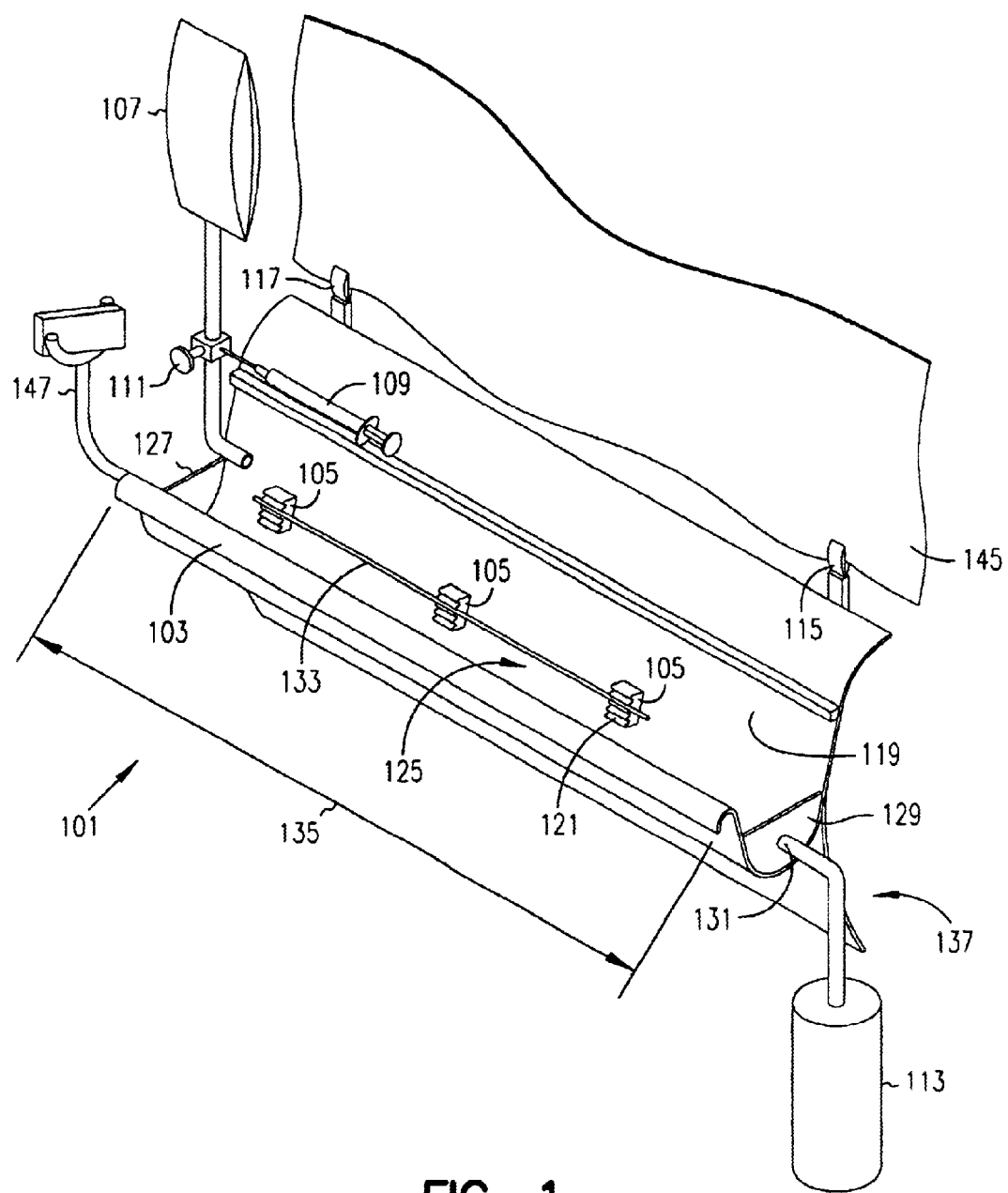
FIG. 1 is an illustration of some embodiments of the guide wire holding apparatus of the present invention.

In the following detailed description of the invention, reference is made to the accompanying drawings which form a part thereof, and in which is shown, by way of illustration, specific embodiments in which the invention may be practiced. In the drawings, like numerals describe substantially similar components throughout the several views. These embodiments are described in sufficient detail to enable those skilled in the art to practice the invention. Other embodiments may be utilized and structural, logical, and electrical changes may be made without departing from the scope of the present invention. The following detailed description is, therefore, not to be taken in a limiting sense, and the scope of the present invention is defined only by the appended claims, along with the full scope of equivalents to which such claims are entitled.

FIG. 1 is an illustration of some embodiments of guide wire holding apparatus 101 of the present invention. Guide wire holding apparatus 101 includes tray 103, one or more raised corrugated areas 105, fluid source 107, syringe 109, valve 111, drainage system 113, and coupling devices 115 and 117. Each of the one or more raised corrugated areas 105 is located on inner surface 119 of tray 103 and include one or more slots, such as slot 121. A reservoir 125 is formed by inner surface 119 and end caps 127 and 129. A flow of fluid provided by fluid source 107 or syringe 109 and controlled by valve 111 partially fills reservoir 125. The height of the fluid in reservoir 125 is partially controlled by the location of cap hole 131. Preferably, cap hole 131 is located at a height that causes guide wire 133, which is shown resting in slot 121, to be slightly submerged when fluid is flowing from fluid source 107 or syringe 109 to drainage system 113.

Tray 103 is preferably fabricated from a disposable material. In one embodiment, tray 103 is fabricated from a plastic, such as a disposable medical grade plastic. Tray 103, when fabricated from a plastic, is economically manufactured using an injection molding process. Alternatively, tray 103 is fabricated from a material that is easily cleaned and sterilized. In one alternate embodiment, tray 103 is fabricated from stainless steel. In another alternate embodiment, tray 103 is fabricated from titanium. Metal shaping and machining processes suitable for use in the fabrication of tray 103 are well known in the art. Tray 103 is not limited to a particular length. The length 135 of tray 103 is selected to be about equal to the length of the catheters and guide wires used in a particular surgical procedure. For example, the guide wires used in an angiography procedure are about 100 centimeters, so length 135 is about 100 centimeters for a tray intended for use in an angiography procedure. Tray 103 preferably has a cross-sectional shape 137 that is curved. A curved cross sectional shape provides for a flow of fluid from fluid source 107 to drainage system 113 that flushes material off the surface of guide wire 133 and along tray 103 into drainage system 113.

Figure 2:
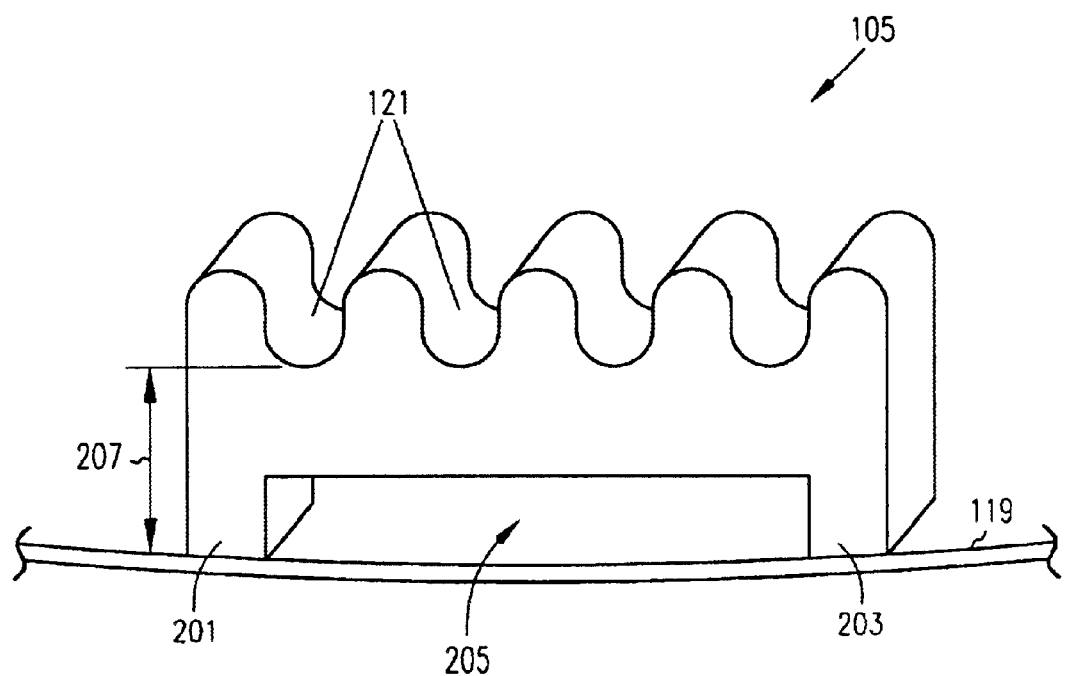
FIG. 2 is an illustration of some embodiment of the raised corrugated areas of the present invention.

FIG. 2 is an illustration of one embodiment of one or more raised corrugated areas 105. Raised corrugated areas 105 include one or more slots 121, legs 201 and 203, and arch 205. Each of the one or more slots is capable of supporting a guide wire. The distance 207 between the bottom of each of the one or more slots 121 and inner surface 119 is sufficient to make a guide wire resting in one of the one or slots 121 easily accessible to a physicians's gloved fingers. In one embodiment, distance 207 is about equal to the diameter of the guide wire. In an alternate embodiment, distance 207 is about 200 millimeters. In one embodiment, raised corrugated areas 105 have legs 201 and 203 connected by arch 205 to enhance the fluid flow along inner surface 119 of tray 103. The exposed surface of legs 201 and 203 are preferably curved. Raised corrugated areas 105 are preferably fabricated as an integral part of tray 103. Alternatively, raised corrugated areas 105 are fabricated as separate units and subsequently attached to inner surface 119 of tray 103.

Referring again to FIG. 1, fluid source 107 is capable of providing fluid to tray 103 for flushing and moisturizing guide wire 133. In one embodiment, fluid source 107 is a plastic bag, such as a sterile source bag, coupled to tray 103 by a plastic tube. The tube material is not limited to plastic, and the tube may be fabricated as an integral part of the bag or fabricated separately from the bag. Any fluid suitable for flushing and moisturizing guide wire 133 may be stored in fluid source 107. In one embodiment, a solution, such as heparinized saline, is stored in fluid source 107.

Syringe 109 is also capable of providing fluid to tray 103 for flushing and moisturizing guide wire 133. Syringe 109 is coupled to fluid source 107 and valve 117. Syringe 109 is capable of withdrawing fluid stored in fluid source 107. After syringe 109 withdraws fluid from fluid source 107, syringe 109 is prepared to discharge fluid into tray 103.

Drainage system 113 receives fluid from fluid source 107 after the fluid passes through reservoir 125. In one embodiment, drainage system 113 is coupled to end cap 129 at cap hole 131. Any system capable of storing or channeling a fluid to an appropriate disposal system is suitable for use as drainage system 113. In one embodiment, drainage system 113 is a plastic bag having a sufficient volume to store the fluid originally contained in fluid source 107.

Coupling devices 115 and 117, in one embodiment, couple tray 103 to surgical drape 145. The coupling devices are preferably selected for easy manipulation by a gloved hand. In one embodiment, coupling devices 115 and 117 are spring clips. To provide for easy alignment of tray 103, the coupling devices have different lengths. Coupling device 115 is preferably longer than coupling device 117, in which case tray 103 is then properly aligned when the coupling devices 115 and 117 are coupled to surgical drape 145 at the same height.

Guide wire holding apparatus 101 provides a flow of liquid over guide wires stored in tray 103, so it is likely that the guide wire will be cleaned as it rests in tray 103. This eliminates the need for cleaning the guide wire by running a wetted gauze bandage along the length of the wire. However, if the guide wire is not sufficiently cleaned while resting in tray 103, the guide wire may simply be pulled through the gauze bandage mounted on arm 147, as the guide wire is being inserted back into the catheter within the patient.

Figure 3:
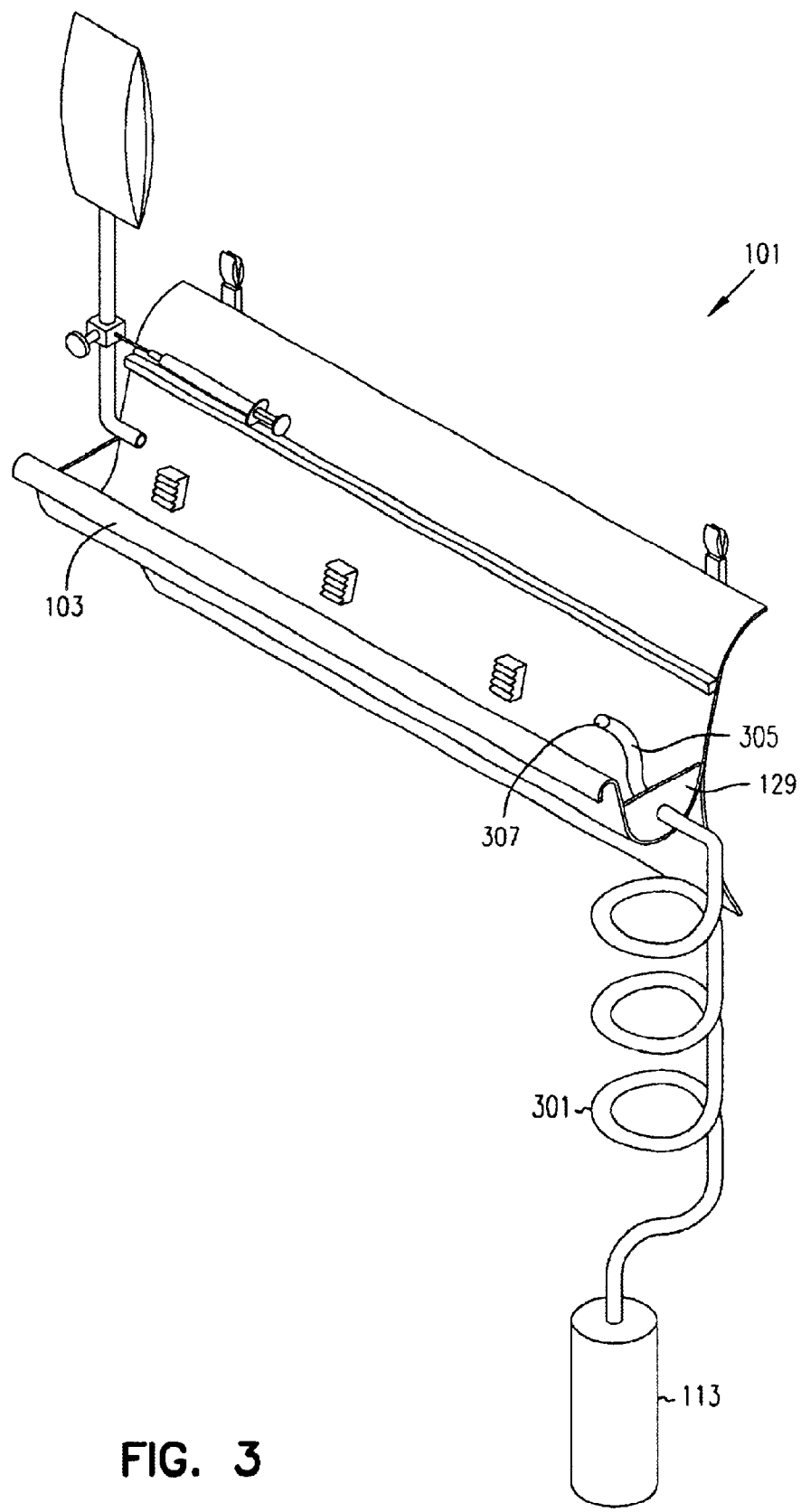
FIG. 3 is an illustration of some alternate embodiments of the guide wire holding apparatus of the present invention.

FIG. 3 is an illustration of some alternate embodiments of the guide wire holding apparatus 101 of the present invention. Guide wire holding apparatus 101, in this embodiment, includes guide wire storage units 301 mounted on end cap 129. For a particular length guide wire, employing guide wire storage units 301 to store a portion of the guide wire allows the use of a shorter tray 103 than if the guide wire storage units were not employed. Alternatively, the use of guide wire storage units 301 to store a portion of the guide wire allows for the use of longer guide wires without altering the length of tray 103. Guide wire storage units 301, in one embodiment, are fluted sleeves 303 fabricated from plastic. The flutes 305, which are provided at the entry point of each of the fluted sleeves 303, facilitate the insertion of the guide wires into the sleeves. The sleeves, when coiled below tray 103, are capable of supporting tray 103, and may also be used to position tray 103 at a table height in the surgical field. The coiled sleeves may also be attached to drainage bag 113 for storing the liquid flushed through the sleeves. By concentrating the fluid in the sleeves, any disturbance to tray 103 will result in little or no spillage.

In use, tray 103 is positioned in the surgical field and coupled to surgical drape 145. Keeping tray 103 in the surgical field permits the retrieval of the guide wires stored in tray 103 with very little effort. Guide wires resting on raised corrugated areas 105 are easily grasped by the fingers of a gloved hand. In addition, a guide wire may be withdrawn from the patient and dropped in tray 103 in the same motion. Thus, the physician's attention is focused exclusively on the patient and the procedure.

Although specific embodiments have been illustrated and described herein, it will be appreciated by those of ordinary skill in the art that any arrangement which is calculated to achieve the same purpose may be substituted for the specific embodiment shown. This application is intended to cover any adaptations or variations of the present invention. Therefore, it is intended that this invention be limited only by the claims and the equivalents thereof.

What is claimed is:

1. An apparatus for holding a guide wire, the apparatus comprising:

a tray having an inner surface; and one or more raised corrugated areas located on the inner surface, wherein the tray includes a reservoir capable of being coupled to a fluid source, the fluid source including a bag containing a saline solution or a syringe coupled to the tray, wherein the syringe is capable of being replenished from a second fluid source, and the second fluid source including a bag capable of containing a saline solution, the bag being coupled to the syringe.

2. An apparatus for holding a guide wire, the apparatus comprising:

a tray having an inner surface;

one or more raised corrugated areas located on the inner surface; and one or more guide wire storage devices coupled to an end of the tray, wherein at least one of guide wire storage devices has a fluted end.

3. An apparatus for holding a guide wire, the apparatus comprising:

a tray having an inner surface;

one or more raised corrugated areas located on the inner surface; and one or more guide wire storage devices coupled to an end of the tray, wherein at least one of guide wire storage devices has a fluted end, and each one of the one or more guide wire storage devices has a spiral shape.

4. An apparatus for holding a guide wire, the apparatus comprising:

a tray having an inner surface;

one or more raised corrugated areas located on the inner surface; and one or more guide wire storage devices coupled to an end of the tray, wherein at least one of guide wire storage devices has a fluted end, and each one of the one or more guide wire storage devices is associated with original packaging material for the one or more guide wire storage devices and the original packaging material is coupled to an end of the tray.

5. An apparatus for holding a guide wire, the apparatus comprising:

a tray having an inner surface;

one or more raised corrugated areas located on the inner surface; and one or more guide wire storage devices coupled to an end of the tray, wherein at least one of guide wire storage devices has a fluted end, and each one of the one or more guide wire storage devices is associated with original packaging material for the one or more guide wire storage devices and the original packaging material is coupled to an end of the tray, and at least one of the guide wire storage devices is coupled to a liquid storage device.

* * * * *

UNITED STATES PATENT AND TRADEMARK OFFICE
CERTIFICATE OF CORRECTION

PATENT NO.    : 6,802,323 B1
DATED         : October 12, 2004
INVENTOR(S)   : Truwit et al.

It is certified that error appears in the above-identified patent and that said Letters Patent is hereby corrected as shown below:

Title page,
Item [56], References Cited, U.S. PATENT DOCUMENTS, in the "McNett" reference, delete "12/1959" and insert -- 10/1959 --, therefor.

Signed and Sealed this

Twelfth Day of July, 2005

JON W. DUDAS
*Director of the United States Patent and Trademark Office*